United States Patent
Prasad (10) Patent No.: US 10,004,679 B2
(45) Date of Patent: Jun. 26, 2018

(54) **COMPOSITIONS OF *AMORPHOPHALLUS KONJAC* AND METHODS FOR THEIR USE IN SKIN CARE**

(71) Applicant: Kodimule Shyam Prasad, Bangalore (IN)

(72) Inventor: Kodimule Shyam Prasad, Bangalore (IN)

(73) Assignee: Vidya Herbs, Inc., Fullerton, CA (US)

(*) Notice: Subject to any disclaimer, the term of this patent is extended or adjusted under 35 U.S.C. 154(b) by 0 days. days.

(21) Appl. No.: 14/975,863

(22) Filed: Dec. 21, 2015

(65) Prior Publication Data
US 2016/0184218 A1    Jun. 30, 2016

Related U.S. Application Data

(60) Provisional application No. 62/097,579, filed on Dec. 29, 2014.

(51) Int. Cl.
*A61K 8/97* (2017.01)
*A61Q 19/08* (2006.01)
*A61Q 19/02* (2006.01)
*A61K 36/888* (2006.01)
*A61K 8/68* (2006.01)
*A61Q 19/00* (2006.01)

(52) U.S. Cl.
CPC .............. *A61K 8/97* (2013.01); *A61K 8/68* (2013.01); *A61K 36/888* (2013.01); *A61Q 19/00* (2013.01); *A61Q 19/02* (2013.01); *A61Q 19/08* (2013.01)

(58) Field of Classification Search
CPC .......... A61K 8/97; A61K 36/888; A61K 8/68; A61Q 19/08; A61Q 19/02; A61Q 19/00
See application file for complete search history.

(56) References Cited

U.S. PATENT DOCUMENTS

| | | | | |
|---|---|---|---|---|
| 5,578,641 A | * | 11/1996 | Jackson | A61K 8/606 424/401 |
| 6,162,906 A | * | 12/2000 | Ohashi | A23G 3/346 426/573 |
| 2010/0255076 A1 | * | 10/2010 | Heber | A61K 8/73 424/450 |

FOREIGN PATENT DOCUMENTS

WO    WO2013/101650    *   7/2013    ............. C08B 15/02

OTHER PUBLICATIONS

Hajime Kimata, Improvement of Atopic Dermatitis and Reduction of Skin Allergic responses by Oral Intake of Konjac Ceramide, 23 Ped. Dermatol. 386 (2006).*
Orawan Tatirat & Sanguansri Charoenrein, Physicochemical Properties of Konjac Glucomannan Extracted from Konjac Flour by a Simple Centrifugation Process, 44 Food Sci. Tech. 2059 (2011).*

* cited by examiner

*Primary Examiner* — Sean M Basquill
(74) *Attorney, Agent, or Firm* — Law Office of Timothy M. Brown (57) ABSTRACT

Compositions derived from an extract of *Amorphophallus konjac* and methods for their use in the treatment of skin conditions. The compositions of the invention find use in maintaining the health of the skin and treating a variety of skin conditions, including wrinkles and fine lines, loss of skin tone, and hyperpigmentation. Without being limited to any particular theory or mechanism, the compositions of the invention treat skin conditions through the inhibition of enzymes, including but not limited to, collagenase, elastase and tyrosinase.

20 Claims, 7 Drawing Sheets

COMPOSITIONS OF *AMORPHOPHALLUS KONJAC* AND METHODS FOR THEIR USE IN SKIN CARE

FIELD OF THE INVENTION

The invention generally relates to compositions derived from herbal extracts. More particularly, the invention relates to compositions derived from *Amorphophallus konjac* (*konjac*) and methods for their use in skin care.

BACKGROUND

The human skin consists of epidermis, corium and tela subcutanea. The epidermis is classified into four layers, namely stratum corneum, stratum granulosum, stratum spinosum and stratum basale. The quantity of ceramides is lower in the stratum corneum of atopic dermatitis, dry skin and the skin of aged individuals. The ceramide content of the skin declines with increasing age (e.g. over 70 years old) with dry appearance in xerotic skin. In addition, there is a marked reduction in the amount of total ceramide in both lesional and non-lesional skin as compared to that of healthy individuals of the same age.

More than just a cosmetic problem, skin aging exposes individuals to significant health risks from infectious microorganisms, UV radiation, defective permeability to topical drugs, and increased susceptibility to contact dermatitis from environmental chemicals. The skin barrier is essential for protecting skin against physical stimuli, thermal challenge and ultraviolet radiation, chemical substances and microbial attack and preventing water loss. The skin needs to be at its functional best in order to properly function (i.e. regulate body temperature, synthesize optimal amounts of vitamin D, and provide critical sensory input from the environment). In vitro studies demonstrate that the moisture content of the stratum corneum is decreased with age. In maturing individuals, the stratum corneum is also susceptible to inflammation and infection. Aging skin also suffers from reduced structural integrity due to lower lipid content, mostly a lower proportion of ceramides. The decline of the ceramide content in aging human skin is possibly due to a decline in enzyme activity that helps to deliver ceramides in usable form to the skin. When aging skin's ability to make ceramides diminishes, as it inevitably does, increased ceramide intake becomes essential.

Synthetic and animal ceramide have been used as materials in cosmetic manufacture. However, it was discovered that Creutzfeldt-Jakob disease may be contracted from eating or using contaminated animal products, especially that of cattle.

What is needed in the art therefore is a safe and effective treatment for improving ceramide content in the skin.

SUMMARY OF THE INVENTION

The inventors of the present disclosure, therefore envisage a cost-effective and safe skin care treatment derived from herbal extracts including *Amorphophallus konjac* ("*A. konjac*" or "*konjac*"). Konjac is a plant of the genus *Amorphophallus*. It is native to warm subtropical to tropical eastern Asia, from Japan and China south to Indonesia. It is a perennial plant growing from a large corm up to 25 cm in diameter. The single leaf is up to 1.3 m across, bipinnate, and divided into numerous leaflets. The flowers are produced on a spathe enclosed by a dark purple spadix up to 55 cm long.

*A. konjac* is a rich source of glucosylceramides which is a glycoside of ceramide, a major spingo (glycol) lipid in plants. Glucosylceramides are essential structural components of mammalian cell membranes and are mostly found at the cell surface, which serve to maintain mammalian skin barrier function through their role as intracellular lipids.

It is an object of the invention to provide a method for skin care in a subject comprising administering to the subject a composition derived from *konjac* in an amount effective to maintain the skin architecture.

It is a further object of the invention to provide a composition derived from a herbal extract for skin care, wherein the extract comprises by weight, about 5% spingolipids containing glucosylceramide.

It is a further object of the invention to provide a method for treating a skin condition in a subject comprising administering to the subject a composition comprising an amount of a composition derived from an extract of *konjac* sufficient to inhibit an enzyme selected from tyrosinase, elastase, collagenase and combinations thereof.

A further object of the invention is to provide a method for treating a skin condition in a subject comprising administering to the subject composition comprising an effective amount of an extract of *konjac*.

A further object of the invention is to provide a composition for skin hydration comprising 3% *konjac* extract and 5% ceramide-base

DEFINITIONS

As used herein, the phrase "*Amorphophallus konjac* material," or "*konjac* material," refers to any portion of the *Amorphophallus konjac* plant, including, but not limited to tubers, seeds, leaves, stems, fruit, fruit skin, flowers, roots, bark, pollen, and combinations thereof.

As used herein, "treating" or "treat" includes: (i) preventing a pathologic condition from occurring (e.g. prophylaxis); (ii) inhibiting the pathologic condition or arresting its development; (iii) relieving the pathologic condition; and/or (iv) diminishing symptoms associated with the pathologic condition.

As used herein, "extract" refers to a substance obtained by extracting a raw material, using a solvent system or physical process.

As used herein, the phrase "skin condition" refers to a pathological condition affecting the skin. Some non-limiting examples of skin conditions include, but are not limited to, wrinkles, fine lines, sagging skin, dryness, xerosis, itching, dermatitis, asteatotic eczema, atopic dermatitis, elastolysis, dermatitis, hand dermatitis, dyshidrotic eczema, stasis dermatitis, seborrheic dermatitis, psoriasis, pityriasis, vitiligo, hyperpigmentation, liver spots, acne, lacerations, eczema, lymphoma of the skin, actinic keratosis, scleroderma, rosacea, an allergic skin disorder, radiation and/or chemotherapy induced mucositis, or a combination thereof.

As used herein, "therapeutically effective amount," or "effective amount," refers to an amount of a substance (or compound) that is sufficient to treat the condition that is intended to be addressed by the administration of the substance or compound to a subject.

The term "subject" as used herein typically refers to a human. In certain embodiments, a subject is a non-human mammal. Exemplary non-human mammals include laboratory, domestic, pet, sport, and stock animals, e.g., mice, cats, dogs, horses, and cows.

The term "about" or "approximately" as used herein usually means within 20%, more preferably within 10%, and most preferably still within 5% of a given value or range. Alternatively, especially in biological systems, the term "about" means within about a log (i.e., an order of magnitude) preferably within a factor of two of a given value.

DETAILED SPECIFICATION

The invention generally relates to compositions derived from herbal extracts and methods for their use in skin care. More particularly, the invention relates to compositions derived from herbal extracts of *Amorphophallus konjac* extract and methods for their use in the treatment of skin conditions.

The compositions of the invention can comprise an extract derived from *Amorphophallus konjac*. Such extracts can be derived from any portion of *Amorphophallus konjac*, including the tubers, seeds, leaves, stems, fruit, flowers, pollen, and combinations thereof. The compositions of the invention can comprise an extract of *Amorphophallus konjac* from tubers. The compositions of the invention can comprise an extract of *Amorphophallus konjac* from leaves. The compositions of the invention can comprise *Amorphophallus konjac* extract from tubers. In a preferred embodiment, the extracts described herein are free of the solvent(s) that is used to obtain the extract from the *Amorphophallus konjac* material. The composition of the invention can comprise a tincture of *Amorphophallus konjac*. The *Amorphophallus konjac* material used to make the compositions described herein can be fresh, dried, rehydrated, powdered, or a combination thereof.

The composition of the present invention may be administered in a therapeutically effective amount. The effective dosage level may be determined depending on a subject's type, severity of the disease, the subject's age and sex, activity of the composition, administration time, administration route, excretion rate, duration of treatment, and other factors known in the medical field. The composition of the present invention may be administered alone or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors, this amount can be easily determined by a person skilled in the art.

The preferred administration dose of the pharmaceutical composition of the present invention may be 0.1 mg/kg/day to 1,000 mg/kg/day.

Another aspect of the invention concerns methods for making the subject compositions. The compositions can comprise an extract of *Amorphophallus konjac*. The compositions of the invention can comprise an extract of *Amorphophallus konjac* obtained from polar or non-polar solvents. The compositions can comprise an extract of *Amorphophallus konjac* that is obtained by ethanol extraction. The compositions can comprise an extract of *Amorphophallus konjac* that is obtained by aqueous extraction. The compositions can comprise an extract of *Amorphophallus konjac* that is obtained by supercritical fluid extraction. As used herein, "supercritical fluid extraction" or "SFE" refers to the process of separating one or more components (extractant) from another (matrix) using supercritical fluids as the extracting solvent. The compositions can be prepared by concentrating a solution obtained from an *Amorphophallus konjac* material such as by extrusion.

The compositions of the invention can comprise *konjac* extract in combination with a pharmaceutically acceptable carrier. Suitable carriers for combining with *konjac* extract are disclosed in Remington's Pharmaceutical Sciences, 19th Edition, Mack Publishing Co., Easton, Pa. 1995, the entire contents of which are incorporated herein by reference in their entirety for all purposes. The pharmaceutical carrier can be an artificial pharmaceutical carrier. The *konjac* extract may be combined with the pharmaceutical carrier at any concentration that permits the *konjac* extract to treat a skin condition as described herein. The concentration of the *konjac* extract can range from 10 µg/mL to about 1,000 µg/mL, including all intervening concentrations at about 1 µg/mL increments. In one non-limiting embodiment, the concentration of *konjac* extract is 100 µg/mL.

The compositions of the present invention may be administered by various routes including but not limiting to topically, orally, buccal, intraaeterially, intravenously, intraperitoneally, sub-lingually, rectally, and by inhalation. The compositions may be in a dosage form that includes but is not limited to powders, pills, tablets, pellets, capsules, thin films, solutions, sprays, syrups, linctuses, lozenges, pastilles, chewing gums, pastes, vaporizers, suspensions, emulsions, ointments, creams, lotions, liniments, gels, drops, topical patches (e.g. adhesive topical patches or transdermal patches), buccal patches, beads, gummies, gels, sols, injections and the like. The compositions of the invention can comprise an extract that is dried to form one or more of the foregoing dosage administration forms.

In some aspects of the invention, the compositions herein include one or more additional constituents to facilitate topical application. The compositions can comprise one or more flow regulating agent(s), including but not limited to, silica (e.g., colloidal silica), silica gel, magnesium trisilicate, or cornstarch. A flow regulating agent may be included to increase flow of the formulation, depending on the application of use. A powder formulation of the compositions may include one or more such flow regulating agent(s). The compositions may further include one or more filler(s), such as titanium dioxide, spray dried lactose, or starch, and may optionally further include one or more excipient(s) such as magnesium stearate to facilitate compression. The compositions for topical administration can comprise a formulation that is an anhydrous absorption base composition. For example, a liquid or semi-liquid anhydrous absorption base of the composition may contain one or more humectant(s) (one or more substance(s) that seals moisture in skin, e.g., act as moisturizers), for example, coconut oil, almond oil, lanolin; one or more surfactant(s) or emulsifier(s), for example, lecithin; and one or more consistency regulator(s) or thickener(s), for example, beeswax.

Oral formulations of the composition can be combined with ordinary foods to enhance the value of the palatability of the composition. For example, the compositions can be mixed with drinks, food supplements, snacks, bars, and virtually any other food, nutritional product or drink that can be supplemented. Thus, the invention specifically includes food substances of specific types combined with the compositions of the invention in specified forms and quantities. The compositions of the invention may be combined with one or more substances to increase the nutritive value of the composition, such substances including, but not limited to, vitamins, minerals, amino acids, proteins, and combinations thereof.

Compositions intended for oral use may be prepared according to any known method, and such compositions may contain one or more agents selected from the group consisting of sweetening agents, flavoring agents, coloring agents, and preserving agents in order to provide commercially viable, pharmaceutically elegant and palatable compositions. Tablets may contain *konjac* extract in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They also may be coated for controlled delivery. For example, a "delayed release" dosage form releases a product or substance at a time other than promptly after administration. Examples of delayed-release systems include repeat-action tablets and capsules, and enteric-coated tablets where timed release is achieved by a barrier coating.

The compositions of the present invention find use in a variety of therapeutic and preventive applications. In some embodiments of the invention, the composition is administered to a subject for restoring skin balance. In other embodiments of the invention, the compositions find use in treating skin conditions. For example, the compositions of the invention may be used in the treatment of hyperpigmentation, loss of skin turgor, loss of skin tonicity, wrinkling, fine lines, sagging skin, dermatitis, psoriasis, and improving skin texture. In some aspects, the inventive compositions are used in lightening the color of the skin (i.e. treating hyperpigmentation), reducing, slowing or preventing the wrinkle formation such as caused by sun damage and aging, increasing skin turgor, increasing skin tone, and combinations thereof. In embodiments of the invention, the compositions are administered as a means for managing skin balance, including but not limited to, reducing wrinkles, skin brightening (e.g. lightening of skin color), moisturizing the skin, and combinations thereof. The term "reduce" as used herein refers to any measurable decrease in a parameter that is produced as a result of administering a composition of the invention, relative to the amount of the parameter that is observed in the absence of such administration. The term "increase" as used herein refers to any measurable increase in a parameter that is produced as a result of administering a composition of the invention, relative to the amount of the parameter that is observed in the absence of such administration.

The compositions of the invention may be administered to modulate one or more enzymes in the treatment of a skin condition or maintenance of the health of the skin. Some non-limiting examples of enzymes that are modulated by the compositions of the invention include, but are not limited to, collagenase, tyrosinase, elastase, and the enzymes involved in ceramide production, regulation and transport. In some embodiments, the compositions of the invention are used to inhibit such enzymes in the treatment of a skin condition. As used herein, the term "inhibit" refers to any measurable decrease in the activity of an enzyme that is brought about by contacting the enzyme, or an enzyme precursor, with an agent.

The compositions of the invention can be administered to a subject to inhibit tyrosinase as a means for lightening the skin tone of the subject. Tyrosinase is a multifunctional, glycosilated, copper containing oxidase and found exclusively in melanocytes. The biosynthetic pathway of tyrosinase is initiated with the hydroxylation of L-tyrosine to 3-4-dihydroxyphenylalanine (L-DOPA) and the oxidation of L-DOPA to o-dopaquinone. This o-dopaquinone is a highly reactive compound and can polymerize spontaneously to form the pigment melanin; this presents a serious aesthetic problem in humans as it results in the darkening of the skin (Briganti et al. 2003). Without being limited to any particular mechanism or theory, the compositions of the invention can be administered to a subject to inhibit tyrosinase and provide a depigmenting (e.g. skin lightening) effect in the subject.

Hyper-pigmented skin is observed in various dermatological conditions namely melasoma, solar lentigines and ephilides (Maeda & Fukuda, 1991). The above mentioned clinical conditions are due to frequent exposure to UV rays, certain drugs and chemicals resulting in skin darkening. Depigmenting agents commonly are prescribed to treat such conditions. The most common skin lightening and depigmentation agents available commercially are kojic acid, arbutin, catechins, hydroquinone and azelaic acid (Maeda & Fukuda, 1996). Some adverse effects of these synthetic compounds are irreversible cutaneous damage and ochronosis, for example. Thus, the compositions of the invention can be used to treat hyperpigmented skin in a subject, including the treatment of melasoma, solar lentigines and ephilides.

The compositions of the invention can be administered to a subject to inhibit elastase as a means for treating wrinkles, fine lines, and loss of skin elasticity. Elastase, a member of the chymotrypsin family of proteases, is responsible primarily for the breakdown of elastin which is an important protein found within the extracellular matrix (ECM). Elastin, due to its unique elastic recoil properties, is vital for giving elasticity to arteries, lungs, ligaments and skin (Kim et al. 2004; Baylac & Racine, 2004; Melzig et al. 2001; Siedle et al. 2002). Elastases can cleave elastin as well as having a broad substrate portfolio including ability to cleave collagen, fibronectin and other ECM proteins (Melzig et al. 2001; Siedle et al. 2002). As with the metalloproteinases, under normal conditions elastase activity is necessary after wounding to degrade foreign proteins within the ECM during phagocytosis by neutrophils to enable tissue repair (Melzig et al. 2001; Siedle et al. 2002). In terms of anti-aging, finding inhibitors of elastase enzymes can be useful to prevent loss of skin elasticity and thus skin's aging.

The compositions of the invention can be administered to a subject to inhibit collagenases and/or metalloproteinases as a means for treating wrinkles, fine lines, and loss of skin elasticity. Matrix metalloproteinases (MMPs) are part of a group of transmembrane zinc containing endopeptidases which include collagenases and gelatinases. Collagenases are metalloproteinases capable of cleaving other molecules found within the cell for example collagenase-2 (MMP-8) can cleave aggrecan, elastin, fibronectin, gelatine and laminin as well as collagen (Raffetto & Khalil, 2008). Collagenase cleaves the X-gly bond of collagen and also synthetic peptides that contain the sequence -Pro-X-Gly-Pro where X is almost any amino acid provided that the amino terminus is blocked (Van Wart & Steinbrink, 1981). Collagenase from the bacteria *clostridium histolyticum* (ChC) also degrades ECM. This bacterial collagenase hydrolyses triple-helical collagen in both physiological conditions and in vitro conditions using synthetic peptides as substrates (Kim et al. 2004; Van Wart & Steinbrink, 1981).

In aspects of the invention, the compositions are administered in the maintenance of the health of the skin. Thus, the compositions of the invention may be administered to maintain skin hydration, function, turgor, tone, and/or color.

The compositions of the invention can be administered to a subject for increasing the moisture content of the skin. Without being limited to any particular theory or mechanism, administering the compositions of the invention to a subject improve the appearance of the skin by fighting dryness, balancing skin tone and improving skin texture. Compositions of the invention can comprise *konjac* extract and ceramide. Such compositions can be combined with any of the other constituents described in the present disclosure. The compositions can comprise *konjac* extract in any ratio that permits the composition to provide any of the therapeutic effects described herein. The compositions can comprise *konjac* extract and ceramide (e.g. a purified ceramide or a ceramide rich material) in a ratio of about 1:1, 1:2, 1:3, 1:4, 1:5, 1:6, 1:7, 1:8, 1:9; 1:10, or any ratio intervening those specifically described here. In one non-limiting embodiment, the ratio of *konjac* extract to ceramide is 1:1.7.

The present disclosure is further described in the light of the following non-limiting examples which are set forth for illustration purpose only and not to be construed for limiting the scope of the disclosure.

EXAMPLE 1

Preparation of *Konjac* Composition 100 kg of *Amorphophallus konjac* (*konjac*) powder was transferred into a cleaned vertical 1.0 KL extractor. The bottom of the extractor comprised a perforated plate on which filtration cloth was fixed. The bottom of the extractor was connected to a transfer pump input and output of the transfer pump was connected to a T bend. One end was connected to the extractor top for circulation of extraction mass while extraction period and the other end of T bend were connected to a receiver tank.

The above mentioned mass was extracted with eight bed volumes of 95-98% v/v ethyl alcohol (aqueous). Extraction was continued at room temperature for about 7-8 hrs with continuous circulation of extract with a transfer pump. After completion of the extraction, the extract was filtered through a 5 micron SS candle filter and clear extract was collected in a receiver tank. The bed was re-extracted by adding 6 bed volumes of 95-98% ethyl alcohol 3 more times at room temperature for about 7-8 hrs and filtered through 5 micron SS candle filter. All the extracts were collected in a receiver tank and combined extract was concentrated in a reactor under vacuum at 80-85° C. until the extract moss TDS reached 60-70 w/w %. The extract moss was dried in a vacuum tray drier at 80-85° C. under vacuum until dry. The yield of the *konjac* composition was about 5.8±0.2 w/w %. The resulting composition was used in the following examples.

EXAMPLE 2

Anti-Tyrosinase Activity of *Konjac* Composition

In Silico Docking Studies of *Konjac* Composition with Enzyme Tyrosinase

Figure 1:
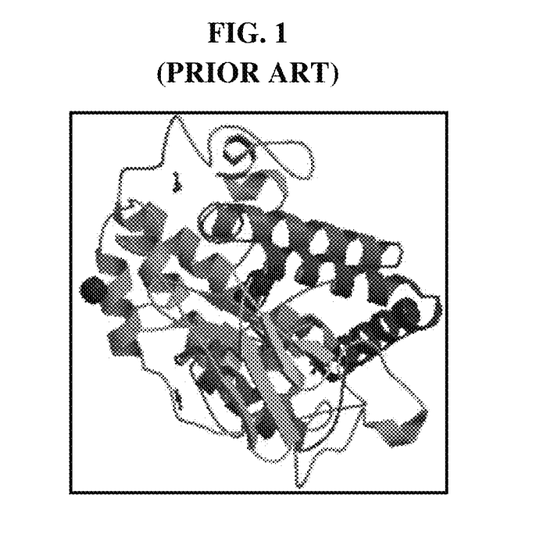
FIG. 1 shows 3D structure of tyrosinase.

AutoDock tools were utilized to generate grids, calculate dock scores and evaluate the conformers of the *konjac* composition bound in the active site of elastase as targets for anti-wrinkle activity. Automated docking is a graphical user interface. AutoDock 4.2 was employed to get docking and binding scores; which is implemented by the Lamarckian genetic algorithm method. The ligand molecules i.e., the *konjac* composition and epigallocatechin gallate (EGCG) were designed and the structure was analyzed using ACD/Chemsketch. The PRODRG server was used to minimize energy of drug compounds and 3D coordinates were prepared. The protein structure file (PDB ID: 1WX2) (FIG. 1) was taken from PDB and was edited by removing the hetero atoms using Python molecule viewer. The grid map was centered at particular residues of the protein and was generated with AutoGrid. As per genetic algorithm all the torsions were allowed to rotate during docking. The Lamarckian genetic algorithm and the pseudo-Solis and Wets methods were applied for minimization, using default parameters (Rodriguez and Infante, 2011).

Figure 2A:
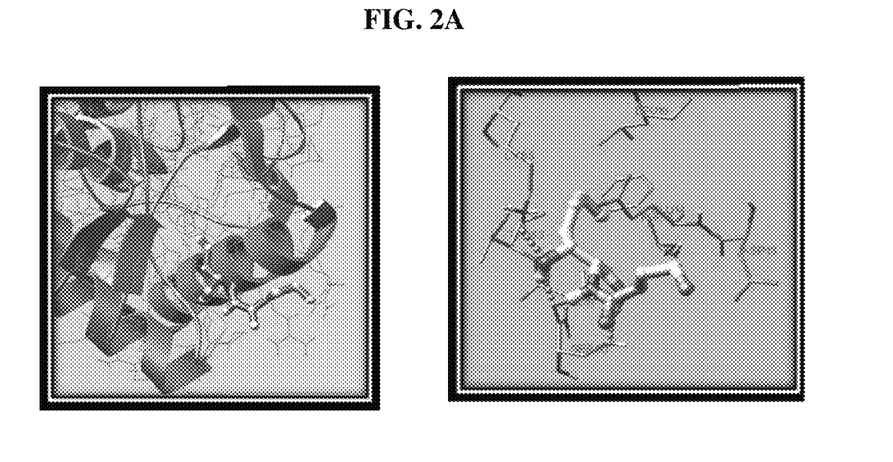
FIG. 2A shows the interaction of a composition derived from *konjac* with tyrosinase.
Figure 2B:
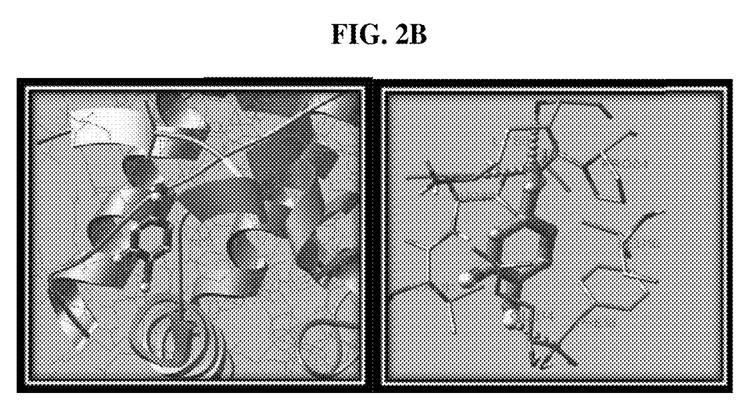
FIG. 2B shows the interaction of kojic acid with tyrosinase.
Figure 3:
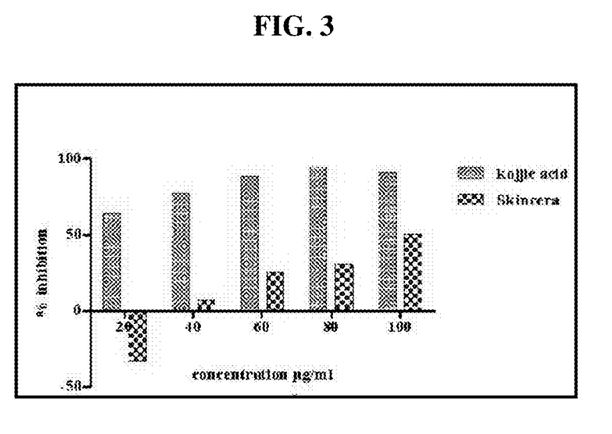
FIG. 3 shows in vitro anti-tyrosinase activity of a composition derived from *konjac*.

The results of molecular docking studies were highly appreciable and showed good interaction of *konjac* composition with the enzymes' active pocket amino acid residues. The molecule was bound with tyrosinase having a minimal binding energy of −6.64 kJmol-1 (Table 1). The interaction was more firm as evident by the formation of 4 hydrogen bonds with tyrosinase as compared to the standard kojic acid (3H-bonds) (FIG. 2). The inhibition of tyrosinase which is involved in melanin production clearly indicated the potential of the *konjac* composition in exhibiting the skin whitening property more convincingly and we further carried out in vitro enzyme assay to confirm its activity.

TABLE 1

Molecular docking of konjac composition with tyrosinase
Thermodynamic parameters

| | Binding energy | Ligand efficiency | Inhibition constant | Intermolecular energy | H-bonds | Interactions |
|---|---|---|---|---|---|---|
| Konjac composition | −6.64 | −0.36 | 65.29 | −8.99 | 4 | Lys5, Ser80 |
| Kojic acid | −5.71 | −0.66 | 13.68 | −7.53 | 3 | Glu14, Thr82, Lys5 |

In Vitro Anti-Tyrosinase Activity of *Konjac* Composition

Mushroom tyrosinase (Prod. No. T7755) and L-DOPA were purchased from Sigma Adrich. Tyrosinase activity was determined by spectrophotometry 4w75 with minor modifications 20 μL of mushroom tyrosinase (1000 U/mL), 20 μL of 0.1 M phosphate buffer (pH 6.8) and 100 μL of the test sample solution (20%) containing 20 μL of *konjac* composition, were mixed (called sample solution with enzyme). We also prepared positive controls of 1mg/mL kojic acid solutions (with water), with enzyme. Twenty 20 μL of 0.85 mM L-DOPA solution as the substrate was added into every sample and blank. These assay mixtures were incubated at 25° C. for 10 min. The amount of dopachrome produced in the reaction mixture was measured at 475 nm.

TABLE 2

Anti-tyrosinase activity of konjac composition
% inhibition of tyrosinase activity

| Concentration in μg/ml | Kojic acid | Konjac extract |
|---|---|---|
| Blank | | |
| 20 | 64.46 | −32.67 |
| 40 | 77.66 | 6.93 |
| 60 | 88.32 | 25.74 |
| 80 | 91.37 | 30.69 |
| 100 | 93.90 | 50.49 |

EXAMPLE 3

Evaluation of Anti-Wrinkle Activity of *Konjac* Composition

In Silico Studies of *Konjac* Composition with Elastase

Figure 4:
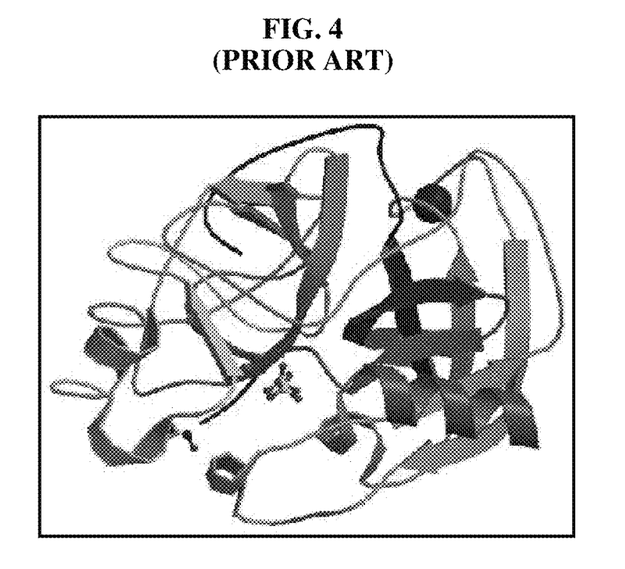
FIG. 4 shows 3D structure of elastase.

AutoDock tools was utilized to generate grids, calculate dock score and evaluate the conformers of the *konjac* composition bound in the active site of Elastase as targets for anti-wrinkle activity. Automated docking is a graphical user interface. AutoDock 4.2 was employed to get docking and binding scores; which is implemented by the Lamarckian genetic algorithm method. The ligand molecules i.e., the *konjac* composition and epigallocatechin gallate (EGCG) were designed and the structure was analyzed using ACD/Chemsketch. The PRODRG server was used to minimize energy of drug compounds and 3D coordinates were prepared. The protein structure file (PDB ID: 1GVK) (FIG. 4) was taken from PDB and was edited by removing the hetero atoms using Python molecule viewer. The grid map was centered at particular residues of the protein and was generated with AutoGrid. As per genetic algorithm all the torsions were allowed to rotate during docking. The Lamarckian genetic algorithm and the pseudo-Solis and Wets methods were applied for minimization, using default parameters (Rodriguez and Infante, 2011).

Figure 5A:
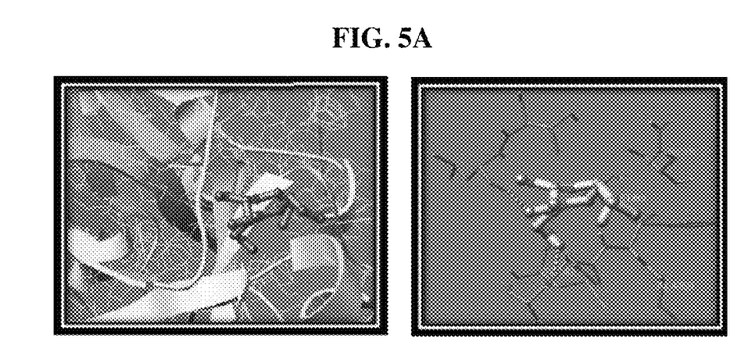
FIG. 5A shows the interaction of elastase with a composition derived from *konjac*.
Figure 5B:
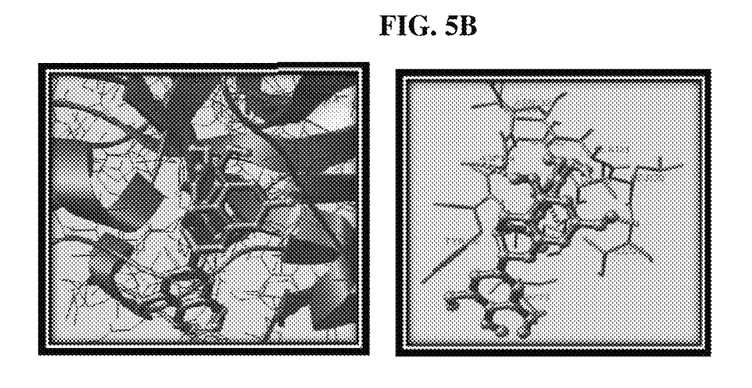
FIG. 5B shows the interaction of elastase with EGCG.

The *konjac* composition exhibited pronounced elastase inhibition activity as evident from the thermodynamic parameters studied. The interaction of molecule with active pocket residues required less binding energy comparable to standard EGCG. The *konjac* composition formed three hydrogen bonds in the active pocket of the protein. The results are depicted in Table 3 (FIG. 5).

TABLE 3

Molecular docking of konjac composition with elastase
Thermodynamic parameters

| Molecule | Binding Energy (kJmol$^{-1}$) | Ligand Efficiency (kJmol$^{-1}$) | Inhibition Constant (μM) | Intermolecular energy (kJmol$^{-1}$) | H-bonds | Interactions |
|---|---|---|---|---|---|---|
| Konjac composition | −7.16 | −0.39 | 30.54 | −9.44 | 3 | Val163, Cys182, Lue130 |
| EGCG | −9.84 | −0.3 | 61.17 | −13.42 | 6 | Met180, Ile129, Asp164, Tyr165, Leu130, Asn178 |

In Vitro Anti-Elastase Activity of *Konjac* Composition

Figure 6:
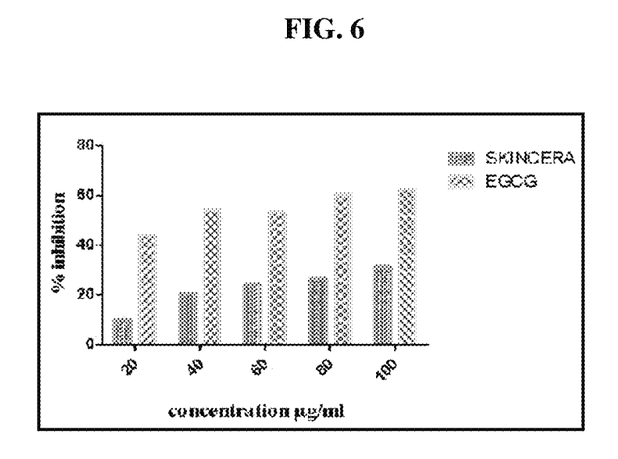
FIG. 6 shows anti-elastase activity of a composition derived from *konjac*.

The assay employed was based on methods from the literature. This assay was performed in 0.2 mM Tris-HCL buffer (pH 8.0). Porcine pancreatic elastase (PE-E.C.3.4.21.36) was dissolved to make a 3.33 mg/mL stock solution in sterile water. The substrate N-succinyl-Ala-Ala-Ala-p-nitroanilide (AAAPVN) was dissolved in buffer at 1.6 mM. The test extracts were incubated with the enzyme for 15 minutes before adding substrate to begin the reaction. The final reaction mixture (250 μL total volume) contained buffer, 0.8 mM AAAPVN, 1 mg/mL PE and 25 mg test extract. EGCG (1 mg/mL) was used as a positive control. Negative controls were performed using water. Absorbance values between 381 and 402 nm (following pre-screen scans) were measured immediately following addition of the substrate and then continuous for 20 minutes. FIG. 6

TABLE 4

Anti-elastase activity of konjac composition
% inhibition of Elastase activity

| Concentration in μg/ml | EGCG | Konjac extract |
|---|---|---|
| Blank | | |
| 20 | 43.98 | 9.801 |
| 40 | 54.36 | 20.471 |
| 60 | 53.32 | 24.194 |
| 80 | 60.37 | 26.427 |
| 100 | 62.45 | 31.266 |

EXAMPLE 4

Anti-Collagenase Activity of *Konjac* Composition

Molecular Docking Studies of *Konjac* Composition with Collagenase

Figure 7:
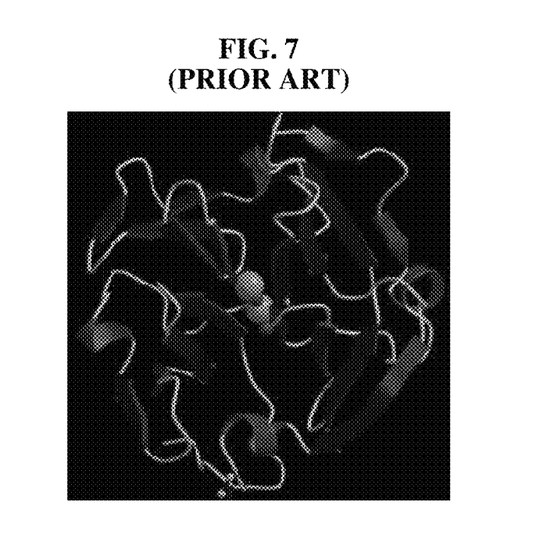
FIG. 7 shows 3D structure of collagenase.

AutoDock tools was utilized to generate grids, calculate dock scores and evaluate the conformers of the *konjac* composition bound in the active site of collagenase as targets for anti-wrinkle activity. Automated docking is a graphical user interface. AutoDock 4.2 was employed to get docking and binding scores; which is implemented by Lamarckian genetic algorithm method. The ligand molecules i.e., the *konjac* composition and epigallocatechin gallate (EGCG) were designed and the structure was analyzed using ACD/Chemsketch. The PRODRG server was used to minimize energy of drug compounds and 3D coordinates were prepared. The protein structure file (PDB ID: 1CGL) (FIG. 7) was taken from PDB and was edited by removing the hetero atoms using Python molecule viewer. The grid map was centered at particular residues of the protein and was generated with AutoGrid. As per genetic algorithm all the torsions were allowed to rotate during docking. The Lamarckian genetic algorithm and the pseudo-Solis and Wets methods were applied for minimization, using default parameters (Rodriguez & Infante, 2011).

Figure 8A:
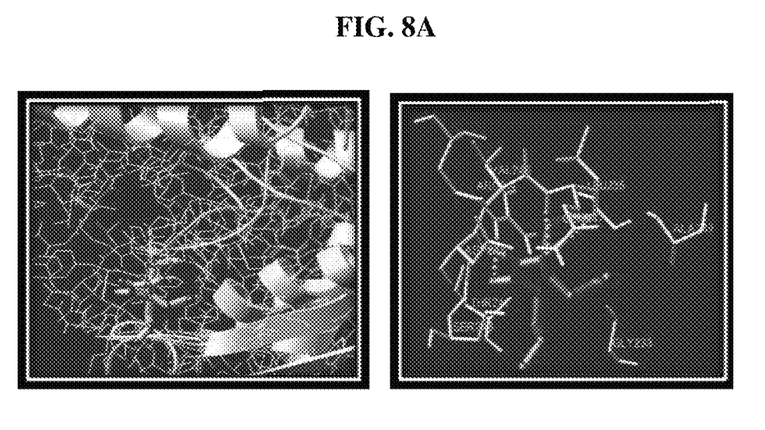
FIG. 8A shows the interaction of collagenase with a composition derived from *konjac*.
Figure 8B:
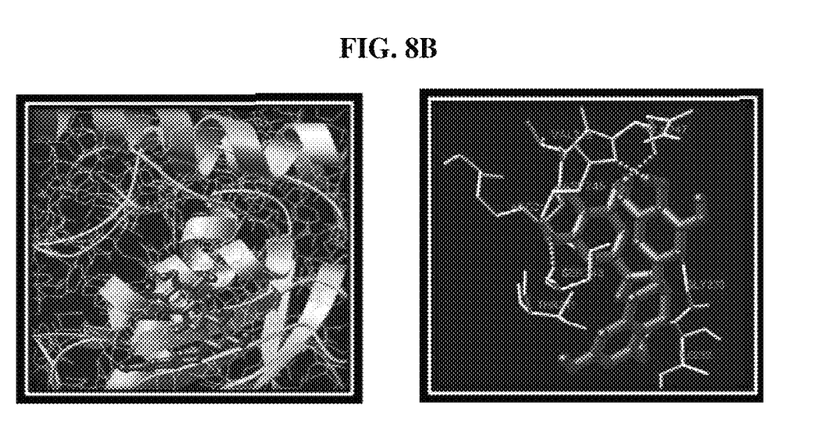
FIG. 8B shows the interaction of collagenase with EGCG.

The *konjac* composition binds very efficiently within the active pocket of collagenase (FIG. 8). The result obtained is comparable to orientation of standard EGCG (Table 5).

TABLE 5

Molecular docking of konjac extract with collagenase
Thermodynamic parameters

| Molecule | Binding Energy (kJmol$^{-1}$) | Ligand Efficiency (kJmol$^{-1}$) | Inhibition Constant (μM) | Intermolecular energy (kJmol$^{-1}$) | H-bonds | Interactions |
|---|---|---|---|---|---|---|
| Konjac | −5.89 | −0.37 | 48.23 | −9.17 | 5 | Arg214, Gln247, Asp245 |
| EGCG | −8.41 | −0.25 | 689.45 | −11.99 | 6 | Asp245, Ser243, Ile232, Gln247 |

In Vitro Anti-Collagenase Activity of *Konjac* Composition

Figure 9:
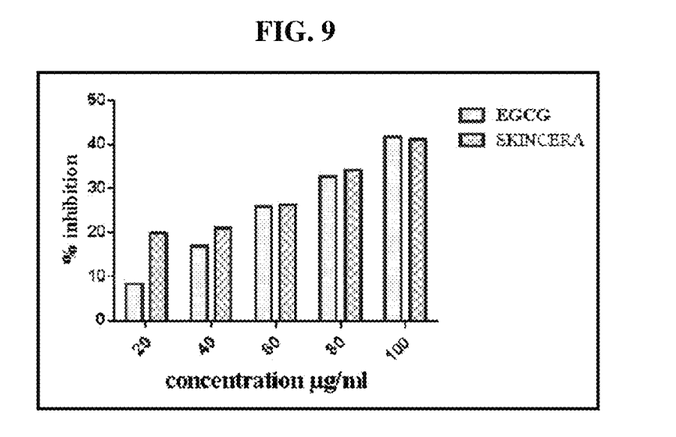
FIG. 9 shows in vitro anti-collagenase activity of a composition derived from *konjac*.

The assay employed was based on spectrophotometric methods reported in the literature. The assay was performed in 50 mM Tricine buffer (pH 7.5 with 400 mM NaCl and 10 mM CaCl2). Collagenase from *Clostridium histolyticum* (ChC-EC.3.4.23.3) was dissolved in buffer for use at an initial concentration of 0.8 units/mL according to the supplier's activity data. The synthetic substrate N-[3-(2-furyl)acryloyl]-Leu-Gly-Pro-Ala (FALGPA) was dissolved in Tricine buffer to 2 mM. The *konjac* composition was incubated with the enzyme in buffer for 15 minutes before adding substrate to start the reaction. The final reaction mixture (150 μL total volume) contained Tricine buffer, 0.8 mM FALGPA, 0.1 units ChC and 20-100 μg test extracts. Negative controls were performed with water. Absorbance at 335 nm was measured immediately after adding substrate and then continuous for 20 minutes. EGCG, 250 μM (0.114 mg/mL) was used as a positive control. FIG. 9

TABLE 6

In vitro anti-collagenase activity of konjac composition
% inhibition of Collagenase activity

| Concentration in μg/ml | EGCG | Konjac extract |
|---|---|---|
| Blank | | |
| 20 | 8.30 | 19.78 |
| 40 | 16.93 | 21.01 |
| 60 | 25.83 | 26.37 |
| 80 | 32.70 | 34.20 |
| 100 | 41.52 | 41.07 |

EXAMPLE 5

The Moisturizing Effects of *Konjac* Composition

The moisturizing effect of *konjac* extract was examined in vitro.

Sample preparation: The *konjac* composition sample solution was prepared by mixing with ceramide-base and distilled water in the ratio 3%, ceramide-base 5% and distilled water 92%.

Condition: Temperature 35° C., RH 40%

1 g of test sample was weighed and added to vessel (3 cm). Samples were weighed 8 hours later. Moisturizing ratio was calculated as follows:

Moisturising Ratio (%)={(Weight at 0 hour−Weight at Time($t$))/Original Weight}×100

Figure 10:
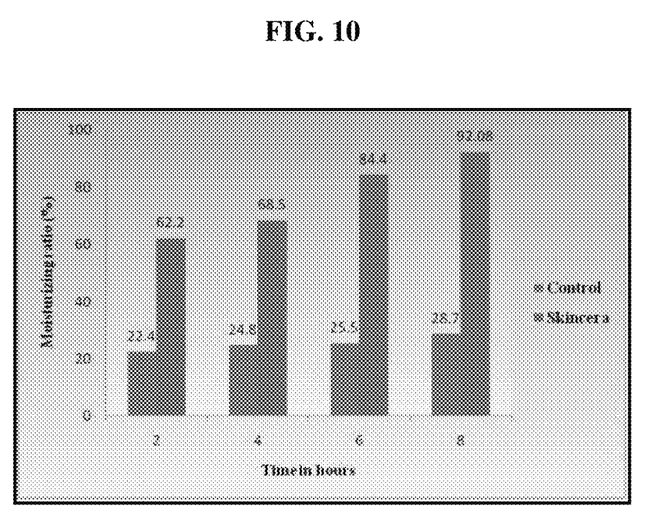
FIG. 10 shows the moisturizing effect of a composition derived from *konjac*.

The *konjac* composition demonstrated superior moisturizing effect with maximum moisturizing ratio of 80.45% as compared to control which is 31.02%. (FIG. 10). Our study shows that the *konjac* composition can be exploited as moisturizer to make the skin look younger and brighter.

REFERENCES

1. Boisnic S, Branchet M C. Interet clinique d'un ingredient alimentaire avisee hydratante:Lipowheat™. Etude randomisee en double aveugle versus placebo. J Med Esth et Chir Derm 2007, 34(136): 239-42.
2. Menon G K, Feingold K R, Moser A H, Brown B E, Elias P M. De novo sterologenesis in the skin. I I. Regulation by cutaneous barrier requirements. J Lipid Res 1985, 26(4): 418-27.
3. Briganti S, Camera E, Picardo M. Chemical and instrumental approaches to treat hyperpigmentation. Pigment Cell Res 2003, 16: 101-110.
4. Maeda K, Fukuda M. Arbutin: mechanism of its depigmenting action in culture. J pharmacol Exp Ther 1996, 276: 765-769. human melanocyte
5. Kim Y, Uyama H, Kobayashi S. Inhibition effects of (+)-catechin-aldehyde polycondensates on proteinases causing proteolytic degradation of extracellular matrix. Biochem Biophys Res Commun 2004, 320:256-261.
6. Raffetto J D, Khalil R A. Matrix metalloproteinases and their inhibitors in vascular remodeling and vascular disease. Biochem Pharmacol 2008, 75:346-359.
7. Van Wart H E, Steinbrink D R. A continuous spectrophotometric assay for *Clostridium histolyticum* collagenase. Anal Biochem 1981, 113:356-365.
8. Baylac S, Racine P. Inhibition of human leukocyte elastase by natural fragrant extracts of aromatic plants. Int J Aromather 2004, 14:179-182.
9. Melzig M F, Loser B, Ciesielski S. Inhibition of neutrophil elastase activity by phenolic compounds from plants. Pharmazie 2001, 56:967-970.
10. Siedle B, Cisielski S, Murillo R, Loser B, Castro V, Klaas C A, Hucke O, Labahn A, Melzig 3999M F, Merfort I. Sesquiterpene lactones as inhibitors of human neutrophil elastase. Bioorg Med Chem 2002, 10: 2855-2861.
11. Narisa Kamkaen, Narong Mulsri, Charoen Treesak. Screening of some tropical vegetables for Anti-Tyrosinase Activity. Thai Pharm Health sci J 2007, 2(1): 15-19
12. Tamsyn Thring S A, Pauline Hili, Declan P N. Anti-collagenase, anti-elastase and anti-oxidant activities of extracts from 21 plants. BMC Compl Alt Med 2009, 9: 27

The invention claimed is:
1. A method of treating a skin condition in a subject in need thereof, the method comprising:
    administering to the subject a composition comprising an *Amorphophallus konjac* tuber extract that is substantially free of glucomannan;
    wherein the extract is made by a process comprising contacting *Amorphophallus konjac* tuber with alcohol to produce a mixture comprising a glucomannan coagulate, and removing the glucomannan coagulate from the mixture thereby producing an extract that is substantially free of glucomannan;

wherein the extract is capable of inhibiting tyrosinase, elastase, collagenase or combinations thereof; and wherein administering the composition treats the skin condition in the subject.

2. The method of claim 1, wherein the skin condition is selected from the group consisting of wrinkling, loss of skin turgor, loss of skin tone, dryness, hyperpigmentation, or combinations thereof.

3. The method of claim 2, wherein the skin condition is hyperpigmentation and administering the composition inhibits tyrosinase in the subject.

4. The method of claim 2, wherein the skin condition is selected from the group consisting of wrinkling, loss of skin tone, and loss of skin torgor and administering the composition inhibits elastase in the subject.

5. The method of claim 2, wherein the skin condition is selected from the group consisting of wrinkling, loss of skin tone, and loss of skin torgor and administering the composition inhibits collagenase in the subject.

6. The method of claim 1, wherein the composition is administered orally or topically.

7. The method of claim 1, wherein the concentration of the extract in the composition is about 100 µg/mL.

8. The method of claim 1, wherein the composition comprises the extract and ceramide in a ratio of about 1:1.7.

9. The method of claim 1, wherein the form of the composition is selected from the group consisting of a powder, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol or injection.

10. A method of treating a skin condition in a subject in need thereof, the method comprising:

administering to the subject a composition comprising an extract of *Amorphophallus konjac* tuber;

wherein the extract is substantially free of glucomannan and is made by a process comprising contacting *Amorphophallus konjac* tuber with alcohol to produce a mixture comprising a glucomannan coagulate, and removing the glucomannan coagulate from the mixture thereby producing an extract that is substantially free of glucomannan; and wherein administering the composition treats the skin condition in the subject.

11. The method of claim 10, wherein the skin condition is selected from the group consisting of wrinkling, loss of skin turgor, loss of skin tone, dryness, hyperpigmentation, or combinations thereof.

12. The method of claim 10, wherein the composition is administered orally or topically.

13. The method of claim 10, wherein the concentration of the extract in the composition is about 100 µg/mL.

14. The method of claim 10, wherein the composition comprises the extract and ceramide in a ratio of about 1:1.7.

15. The method of claim 10, wherein the form of the composition is selected from the group consisting of a powder, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol and injection.

16. A composition for treating a skin condition, the composition comprising *konjac* extract and ceramide in a ratio of about 1:1.7, wherein the extract is substantially free of glucomannan and is made by a process comprising contacting *Amorphophallus konjac* tuber with alcohol to produce a mixture comprising a glucomannan coagulate, and removing the glucomannan coagulate from the mixture thereby producing an extract that is substantially free of glucomannan.

17. The composition of claim 16, further comprising a material selected from the group consisting of colloidal silica, silica gel, magnesium trisilicate, or combinations thereof.

18. The method of claim 1, wherein the glucomannan coagulate is removed by filtration and the extract is a filtrate.

19. The method of claim 10, wherein the glucomannan coagulate is removed by filtration and the extract is a filtrate.

20. The composition of claim 16, wherein the glucomannan coagulate is removed by filtration and the extract is a filtrate.

* * * * *